(12) United States Patent
Shinkawa et al.

(10) Patent No.: US 11,024,329 B2
(45) Date of Patent: Jun. 1, 2021

(54) WORD REPETITION IN SEPARATE CONVERSATIONS FOR DETECTING A SIGN OF COGNITIVE DECLINE

(71) Applicant: INTERNATIONAL BUSINESS MACHINES CORPORATION, Armonk, NY (US)

(72) Inventors: Kaoru Shinkawa, Tokyo (JP); Yasunori Yamada, Saitama (JP)

(73) Assignee: INTERNATIONAL BUSINESS MACHINES CORPORATION, Armonk, NY (US)

(*) Notice: Subject to any disclaimer, the term of this patent is extended or adjusted under 35 U.S.C. 154(b) by 212 days.

(21) Appl. No.: 15/938,693

(22) Filed: Mar. 28, 2018

(65) Prior Publication Data
US 2019/0304484 A1   Oct. 3, 2019

(51) Int. Cl.
| | |
|---|---|
| A61B 5/00 | (2006.01) |
| G10L 25/66 | (2013.01) |
| G10L 15/02 | (2006.01) |
| G10L 15/22 | (2006.01) |
| G10L 15/26 | (2006.01) |

(52) U.S. Cl.
CPC .......... *G10L 25/66* (2013.01); *A61B 5/4076* (2013.01); *A61B 5/4088* (2013.01); *A61B 5/4842* (2013.01); *G10L 15/02* (2013.01); *G10L 15/22* (2013.01); *G10L 15/26* (2013.01)

(58) Field of Classification Search
CPC .... A61B 5/4088; A61B 5/4842; A61B 5/4076
See application file for complete search history.

(56) References Cited

U.S. PATENT DOCUMENTS

| | | | | |
|---|---|---|---|---|
| 8,521,823 | B1* | 8/2013 | Sheinberg | G06Q 10/107 709/206 |
| 8,612,211 | B1* | 12/2013 | Shires | G10L 15/26 704/9 |
| 10,213,145 | B1* | 2/2019 | McNair | A61B 5/165 |
| 2001/0027204 | A1* | 10/2001 | Herting | A61K 31/42 514/380 |

(Continued)

OTHER PUBLICATIONS

Forbes-McKay, K. E., & Venneri, A. (2005). Detecting subtle spontaneous language decline in early Alzheimer's disease with a picture description task. Neurological sciences, 26(4), 243-254.*

(Continued)

*Primary Examiner* — Bryan S Blankenagel
(74) *Attorney, Agent, or Firm* — Tutunjian & Bitetto, P.C.; Randall Bluestone

(57) ABSTRACT

A computer-implemented method for supporting detection of a sign of cognitive decline is disclosed. In the method, two or more sets of conversation data of a target individual are obtained. The method includes combining at least two sets of the conversation data corresponding to plural different days to generate a combined set and extracting one or more linguistic features that represent vocabulary richness from at least the combined set. A feature that characterizes word repetitiveness in conversations across the plural different days of the target individual is calculated from the one or more linguistic features. The feature that characterizes the word repetitiveness is output.

17 Claims, 13 Drawing Sheets

(56) References Cited

U.S. PATENT DOCUMENTS

| | | | | |
|---|---|---|---|---|
| 2009/0099848 | A1* | 4/2009 | Lerner | G10L 17/26 704/271 |
| 2015/0154263 | A1* | 6/2015 | Boddhu | G06F 16/2465 707/737 |
| 2016/0262613 | A1 | 9/2016 | Klin et al. | |
| 2017/0344572 | A1* | 11/2017 | Peterson | G06F 16/93 |
| 2018/0143989 | A1* | 5/2018 | Nomula | G06F 16/3329 |
| 2019/0150823 | A1* | 5/2019 | Hinton | G06Q 10/00 |
| 2019/0328301 | A1* | 10/2019 | Xu | A61B 5/14546 |

OTHER PUBLICATIONS

Bayles, K. A. (1982). Language function in senile dementia. Brain and language, 16(2), 265-280.*

Weiner, "Manual and Automatic Transcriptions in Dementia Detection from Speech", Interspeech, Aug. 2017, pp. 3117-3121.

Manfredi, "Smartphones Offer New Opportunities in Clinical Voice Research", The Voice Foundation Journal of Voice, vol. 31, Issue 1 Jan. 2017, pp. 111.e1-111.e7.

Kawano, "The Delayed Word Recall Task Using ADAS-Jcog Word Booklet Effectively Divides Patients with Mild Cognitive Impairment from Normal Elderly People", Japanese Journal of Geriatrics, vol. 44, No. 4, Jul. 2007, pp. 490-496.

Fraser, "Linguistic Features Identify Alzheimer's Disease in Narrative Speech", Journal of Alzheimer's Disease 49, 2016, pp. 407-422.

Cook, "Verbal Repetition in People with Mild-to-Moderate Alzheimer Disease: A Descriptive Analysis from the VISTA Clinical Trial", Alzheimer Dis Assoc Disord, vol. 23, No. 2, Apr.-Jun. 2009, pp. 146-151.

Bucks, "Analysis of Spontaneous, Conversational Speech in Dementia of Alzheimer Type: Evaluation of an Objective Technique for Analysing Lexical Performance", Aphasiology, vol. 14, No. 1, Aug. 2010, pp. 71-91.

Shinkawa, "Word Repetition in Separate Conversations for Detecting Dementia: A Preliminary Evaluation of Data of Regular Monitoring Service", AMIA 2018 Informatics Summit, Mar. 2018, pp. 1-10.

Grace Period Disclosure—Shinkawa, "Word Repetition in Separate Conversations for Detecting Dementia: A Preliminary Evaluation of Data of Regular Monitoring Service", AMIA 2018 Informatics Summit, Mar. 2018, pp. 1-10.

* cited by examiner

Once upon a time, there was an old man and his wife in a village. One day, the old man went to the mountain for lawn mowing, and his wife went to do the washing to the river. ~ 200

⬇ WORD SEGMENTATION/ MORPHOLOGICAL ANALYSIS once/upon/a/time/,/there/be/an/old/man/and/his/wife/in/a/village/./one/day/,/the/old/man/go/to/the/mountain/for/lawn/mow/,/and/his/wife/go/to/do/wash/to/the/river/. ~ 210

⬇ PART-OF-SPEECH FILTERING once/upon/time/there/be/old/man/and/his/wife/village/one/day/old/man/go/mountain/lawn/mow/and/ his/wife/do/wash/river ~ 220

⬇ STOP WORD FILTERING once/upon/time/old/man/his/wife/village/one/day/old/man/go/mountain/lawn/mow/his/wife/do/wash/river ~ 230

FIG. 4

| word | : | multiplicity |
|---|---|---|
| once | : | 1 |
| upon | : | 1 |
| time | : | 1 |
| old | : | 2 |
| man | : | 2 |
| his | : | 2 |
| wife | : | 2 |
| village | : | 1 |
| one | : | 1 |
| day | : | 1 |
| go | : | 2 |
| mountain | : | 1 |
| lawn | : | 1 |
| mow | : | 1 |
| do | : | 1 |
| wash | : | 1 |
| river | : | 1 |

WORD REPETITION IN SEPARATE CONVERSATIONS FOR DETECTING A SIGN OF COGNITIVE DECLINE

STATEMENT REGARDING PRIOR DISCLOSURES BY THE INVENTOR OR A JOINT INVENTOR

"Grace period disclosures" were made public on Jan. 13, 2018 and Mar. 12, 2018, respectively, less than one year before the filing date of the present U.S. patent application. The publication was entitled "Word Repetition in Separate Conversations for Detecting Dementia: A Preliminary Evaluation on Data of Regular Monitoring Service" and the joint authors of this publication were Kaoru Shinkawa and Yasunori Yamada, who are also named as joint-inventors of the invention described and claimed in the present patent U.S. application. This publication was published at the web site of AMIA 2018 Informatics Summit (https://informaticssummit2018.zerista.com/event/member/470366) on Jan. 13, 2018. An oral presentation based on this publication was also made by Ms. Kaoru Shinkawa as presenter on Mar. 12, 2018 at AMIA 2018 Informatics Summit held in San Francisco at Mar. 12-15, 2018.

BACKGROUND

Technical Field

The present disclosure, generally, relates to diagnosis support technology, more particularly, to techniques for supporting detection of signs of cognitive decline, which may be associated with dementia, neurodegenerative diseases such as Alzheimer's disease, etc.

Description of the Related Art

As the worldwide elderly population increases, the incidence of dementia is becoming an increasingly serious health and social problem. Early diagnosis and intervention have been increasingly recognized as a possible way of improving dementia care. According to recent advances in digital devices such as tablets, mobile phones, and IoT sensors, monitoring technology capable of detecting early signs of dementia in everyday situations has great potential for supporting earlier diagnosis and intervention. Although there are already several projects and services for monitoring the health of elderly persons with frequent data collection by using mobile applications, it has not been explored sufficiently how to exploit the data collected on a daily basis to detect dementia.

The short-term memory loss associated with dementia makes ordinary conversation difficult because of language dysfunctions such as word-finding and word-retrieval difficulties. These language dysfunctions have typically been characterized by using linguistic features. Conventionally, linguistic features extracted from speech data while individuals perform neuropsychological tests is used to estimate the risks of the neurodegenerative diseases and cognitive decline. These linguistic features typically focused on vocabulary richness, repetitiveness, syntactic complexity, etc.

Syntactic complexity is closely associated with the incidence of dementia. Syntactic complexity has been measured in various ways, such as the mean length of sentences, "part-of-speech" frequency, and dependency distance. Another category is vocabulary richness that measures lexical diversity, which tends to reduce in dementia cases. The vocabulary richness has been calculated by three typical measures: type-token ratio (TTR), Brunet's index (BI), and Honoré's statistic (HS) (R. S. Bucks, S. Singh, J. M. Cuerden, and G. K. Wilcock. Analysis of spontaneous, conversational speech in dementia of Alzheimer type: Evaluation of an objective technique for analysing lexical performance. Aphasiology, 14(1):71-91, 2000. A. and Honoré. Some simple measures of richness of vocabulary. Association for literary and linguistic computing bulletin, 7(2): 172-177, 1979). Note that most of the conventional linguistic features are extracted from one shot data that is obtained during doctor's neuropsychological test, for example.

However, accuracy for estimating the risk of neurodegenerative diseases and cognitive decline is not enough. There is still a need for developing novel technology to improve the estimation performance of the risk of the neurodegenerative diseases and the cognitive decline.

SUMMARY

According to an embodiment of the present invention a computer-implemented method for supporting detection of a sign of cognitive decline is provided. The method includes obtaining two or more sets of conversation data of a target individual. The method also includes combining at least two sets of the conversation data corresponding to plural different days to generate a combined set; and extracting one or more linguistic features that represent vocabulary richness from at least the combined set. The method further includes calculating a feature that characterizes word repetitiveness in conversations across the plural different days of the target individual from the one or more linguistic features. The method further includes outputting the feature.

According to the method of the embodiment of the present invention, the feature suitable to detect a sign of cognitive decline can be computed from the conversation data of the target individual. Leveraging the specially designed feature can lead to a performance improvement for detecting the sign of the cognitive decline. Furthermore, it is expected to reduce the computational resources by enriching features that can be used to detect the sign of the cognitive decline.

In a preferable embodiment, the feature is calculated by using a weight for evaluating the linguistic feature depending upon a separation between conversations corresponding to the at least two sets combined. In a further preferable embodiment, the one or more linguistic features include a first linguistic feature extracted from the combined set and one or more other linguistic features each extracted from one of the two or more sets of the conversation data. In the typical monitoring service, practically, it is difficult to obtain conversation data at predetermined regular intervals due to user's circumstances. By weighting the linguistic feature depending upon the separation, the sets of the conversation data that has such variation can be utilized without being wasted, and can be evaluated by taking such variation of the separation into account.

In a further preferable embodiment, the feature is calculated as a weighted sum of reciprocal numbers of the first linguistic feature and the one or more other linguistic features. By defining the reciprocal number of the linguistic feature that represents vocabulary richness as a feature, word repetition in the single or combined conversational data can be captured with higher resolution.

In a preferable embodiment, the weight is defined as a weight function of the separation with a parameter and the weight function is optimized by preparing one or more training samples, each of which includes one or more sample sets of conversation data of a participant and a label regarding the cognitive decline. The weight function is also optimized by enumerating a plurality of combinations based on the one or more training samples, in which each combination includes at least two sample sets of the conversation data corresponding to plural different days of the same participant with a label for the at least two sample set. The weight function is further optimized by finding an optimal value of the parameter of the weight function based on the plurality of the combinations by maximizing discriminative power given by the feature, which is evaluated by using the corresponding label in each combination. Thereby, the parameter of the weight function can be determined based on training samples.

Computer systems and computer program products relating to one or more aspects of the present invention are also described and claimed herein.

Additional features and advantages are realized through the techniques of the present invention. Other embodiments and aspects of the invention are described in detail herein and are considered a part of the claimed invention.

BRIEF DESCRIPTION OF THE DRAWINGS

The subject matter, which is regarded as the invention, is particularly pointed out and distinctly claimed in the claims at the conclusion of the specification. The foregoing and other features and advantages of the invention are apparent from the following detailed description taken in conjunction with the accompanying drawings in which:

FIG. 4 depicts a schematic depicting a process for a conversation document as preprocessing for calculating the feature according to the exemplary embodiment of the present invention;

FIG. 5 depicts a schematic depicting a calculation of a linguistic feature that represents a vocabulary richness as preprocessing for calculating the feature according to the exemplary embodiment of the present invention;

DETAILED DESCRIPTION

Now, the present invention will be described using particular embodiments, and the embodiments described hereafter are understood to be only referred as examples and are not intended to limit the scope of the present invention.

One or more embodiments according to the present invention are directed to computer-implemented methods, computer systems and computer program products for supporting detection of a sign of cognitive decline, in which a novel feature that characterizes word repetitiveness in conversations across plural different days of a target individual is calculated from at least two sets of conversation data of the target individual. One or more other embodiments according to the present invention are also directed to computer-implemented methods, computer systems and computer program products for optimizing a feature function that is used for calculating a novel feature to support detection of a sign of cognitive decline, in which the feature function is optimized based on one or more training samples, each of which includes one or more sample sets of conversation data of a participant and a label regarding the cognitive decline.

Hereinafter, referring to a series of FIGS. 1-8, a computer system and computer-implemented methods for supporting detection of a sign of cognitive decline by utilizing a novel feature according to an exemplary embodiment of the present invention will be described. Then, referring to a series of FIGS. 9-12, experimental studies on the novel feature according to the exemplary embodiment of the present invention will be described. Finally, referring to FIG. 13, a hardware configuration of a computer system according to one or more embodiments of the present invention will be described.

Exemplary Embodiment

Now, referring to a series of FIGS. 1-8, a diagnosis support system and a computer-implemented method for supporting detection of an early sign of cognitive decline, which may be associated with dementia and neurodegenerative diseases such as Alzheimer's disease, etc., are described.

Figure 1:
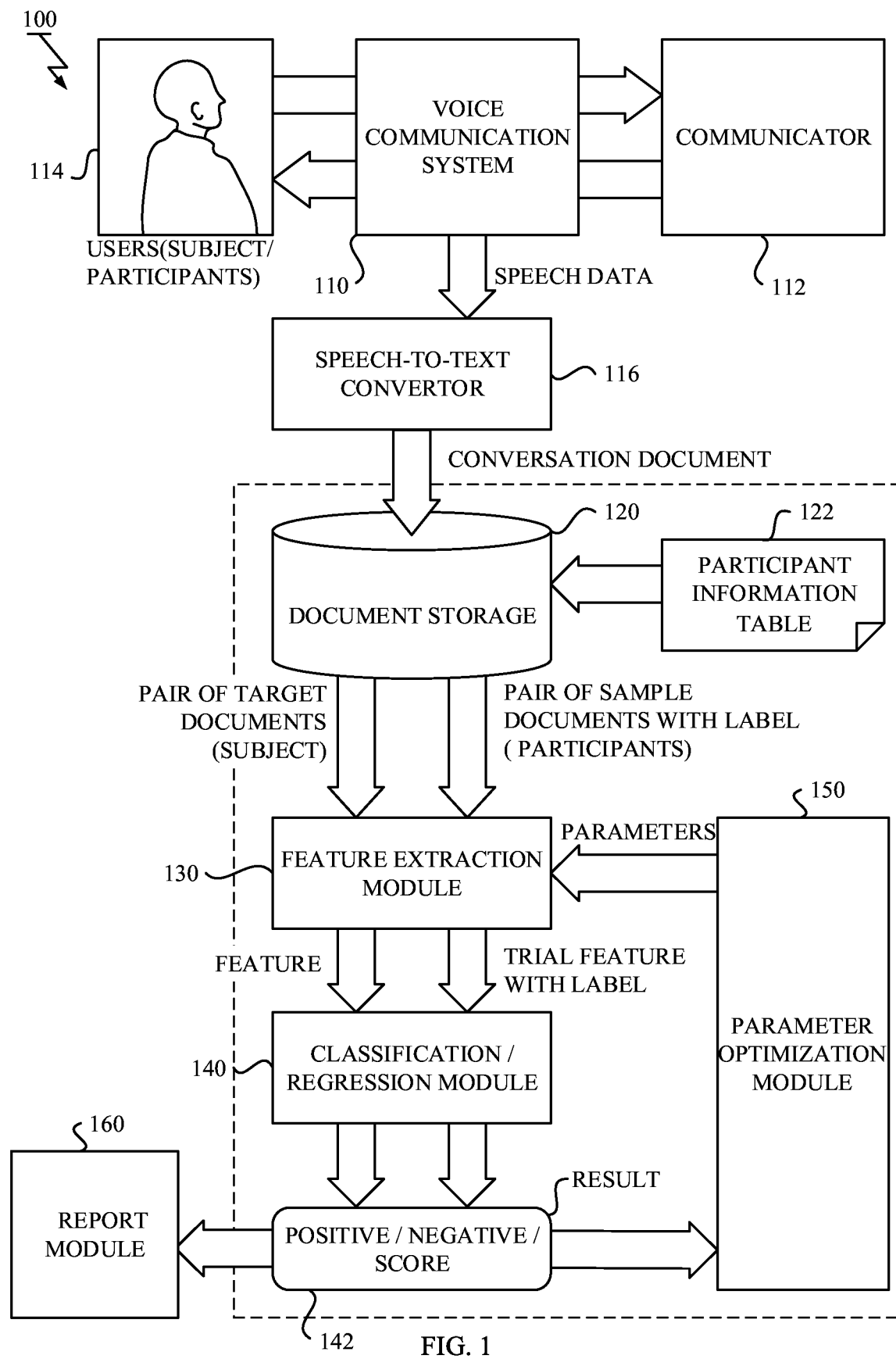
FIG. 1 illustrates a block diagram of a diagnosis support system for cognitive decline according to an exemplary embodiment of the present invention.

FIG. 1 illustrates a block diagram of a diagnosis support system 100 for cognitive decline. As shown in FIG. 1, the diagnosis support system 100 may include a voice communication system 110 that mediates the exchange of the voice communications between a communicator 112 and a user 114; a speech-to-text convertor 116 that converts speech signal transmitted through the voice communication system 110 to a text; and a document storage 120 that stores a text transcribed by the speech-to-text convertor 116 as a conversation document, which is a set of conversation data recorded for the user 114 during a conversation with the communicator 112.

The voice communication system 110 may be any one of known systems that can mediate the exchange of at least voice communications between at least two parties (e.g., the communicator 112 and the user 114). Such system may include a telephone exchange system, a VoIP (Voice over Internet Protocol) phone system, a voice chat system and a video call system, to name but a few. Note that the voice communication system 110 is schematically depicted in FIG. 1 as one box: however, the voice communication system 110 includes facilities, cables, devices, etc., which may include terminal devices for the two parties such as a feature phone, a smart phone, a tablet computer, a smart speaker, etc.

The user 114 may be a subject who is a target individual of detection of early signs of the cognitive declines or a participant who participates in contributions to improve the detection performance of the system 100, according to a registration of the user 114 to the diagnosis support system 100. The user 114 may be registered as either of the subject (a recipient of diagnosis support service whose healthy status is unknown) and the participant (e.g., a healthy control or a patient), or as both (a recipient of the service who is currently considered healthy).

The information of the participants is managed in a participant information table 122. When registering to the system or updating the user information in the system, the participant or his/her family may declare whether he/she is suffering from cognitive decline or is diagnosed as being healthy. Furthermore, the family may declare the severity of the cognitive decline when the participant is suffering from the cognitive decline. The participant information table 122 may hold, for each participant, a label indicating whether the participant is declared as a healthy control or a patient. In a preferable embodiment, the participant information table 122 may further include severity information for each participant suffering from the cognitive decline.

The communicator 112 may be a human communicator or a family member of the user 114 who may call the user 114 on a regular or occasional basis to have a daily conversation for certain period such as several minutes. Alternatively, the communicator 112 may be a computational system such as a voice chat bot that can mimic a human communicator.

The speech-to-text convertor 116 is configured to convert from speech signal transferred from the voice communication system 110 to a text. In a particular embodiment, the speech signal of at least the user 114 may be transferred to the speech-to-text convertor 116. Each text transcribed from the speech signal recorded during a single conversation is stored in the document storage 120 as a conversation document in association with identification information (ID) of the user 114 and timestamp (or dates). The conversation document obtained from the participant may be stored as sample conversation documents in further association with a label regarding the cognitive decline, which may obtained from the participant information table 122.

In the described embodiment, the voice communication system 110 is used to acquire speech signals transmitted therethrough by intervening in the remote voice communication between the user 114 and the communicator 112. However, the way of acquiring the speech signals between the user 114 and the communicator 112 is not limited to the specific way. In other embodiments, instead of using the voice communication system 110 that mediates the exchange of the remote voice communication, there may be an apparatus such as a smart speaker and a recording device that can acquire sound signal of the surrounding environment where the user 114 and the communicator 112 perform face-to-face conversations in everyday life situations. In such case, the speech signal of the user 114 can be identified by the speaker identification/diarization techniques and selectively transferred to the speech-to-text convertor 116.

Referring further to FIG. 1, the diagnosis support system 100 includes a feature extraction module 130 that performs novel feature extraction according to the exemplary embodiment and a classification/regression module 140 that infers a health state of the user 114 based on the result 142 from the feature extraction module 130.

The feature extraction module 130 is configured to calculate a novel feature G that characterizes word repetitiveness in conversations across plural different days based, at least in part, on a pair of conversation documents of the same user 114 that stored in the document storage 120. The feature extraction module 130 picks up the pair of the conversation documents $D_i$, $D_j$ that correspond to plural different days and combines the conversation documents $D_i$, $D_j$ to generate a combined conversation document $D_{ij}$. The combined conversation document $D_{ij}$ can be created by simply concatenating the paired documents $D_i$, $D_j$. The feature extraction module 130 extracts at least linguistic feature $R_{ij}$ that represents vocabulary richness from the combined conversation document $D_{ij}$, and calculates the feature G based, at least in part, on the extracted linguistic feature $R_{ij}$. Note that in the described embodiment, the combined conversation document is generated from the pair of the conversation documents $D_i$, $D_j$. However, the number of documents to generate the combined conversation document may not be limited to two. In other embodiment, three or more conversation documents can be combined.

In a preferable embodiment, one or more other linguistic features $R_k$ that also represent vocabulary richness are extracted from one or more single conversation documents $D_k$, which may include the two conversation documents $D_i$, $D_j$ to be combined, and the feature G is calculated based on the one or more other linguistic features $R_k$ in combination with the linguistic feature $R_{ij}$. In the preferable embodiment, the feature G is calculated by using one or more weights that are used for evaluating the linguistic features $R_k$, $R_{ij}$ depending upon a separation T between conversations that corresponds to the two conversation documents $D_i$, $D_j$ combined. The separation T can be calculated based on the timestamps or the dates associated with the two conversation documents $D_i$, $D_j$.

The linguistic feature R that represents vocabulary richness in the conversation document may be any one of Honoré Statics (HS), a type-token ratio (TTR), and Brunet's index (BI). The Honoré statistic (HS) can be preferably used as the linguistic feature R for each conversation document. More detail about the feature extraction will be described later.

The classification/regression module 140 is configured to infer a health state of the user 114 based on the novel feature G extracted by the feature extraction module 130. The classification/regression module 140 may be based on any machine learning models, including a classification model, a regression model, etc.

When the classification/regression module 140 is based on the classification model, the health state inferred by the classification/regression module 140 may be represented by a class indicating whether or not there is any signs of the cognitive decline (e.g., positive/negative for the binary classification) or the degree of the risk of the cognitive decline (e.g., levels of severity (no risk/low risk/high risk) for multinomial classification). When the classification/regression module 140 is based on the regression model, the health state inferred by the classification/regression module 140 may be represented as a value that measures the degree of the risk of the cognitive decline (e.g., severity score). Depending on the granularity of the inference requested, appropriate label information of the sample conversation document is prepared.

In a particular embodiment, to infer the health state of the user 114, the classification/regression module 140 can utilizes the feature G extracted by the feature extraction module 130 solely or in combination with one or more other features. Such other feature may include any of known features, including features relating to vocabulary richness (TTR, BI, HS), features relating to repetitiveness (frequency of repeated words and phrases, sentence similarities), features relating to syntactic complexity (mean length of sentences, "part-of-speech" frequency, and dependency distance).

The diagnosis support system 100 shown in FIG. 1 may further include a parameter optimization module 150 that optimizes one or more parameters of the feature extraction module 130 based on the result 142 inferred by the classification/regression module 140 and a report module 160 that reports the result 142 inferred by the classification/regression module 140 to the user 114 or his/her family via an appropriate communication tool such as e-mail, an instant message, a web site, a mobile application, etc. The diagnosis support system 100 may have multiple modes of operation, including a learning mode where the parameter optimization module 150 operates and an inference mode where the report module 160 operates.

In the document storage 120, a collection of training samples, each of which includes one or more sample conversation documents obtained from a participant user 114 and a label regarding the cognitive decline of the participant user 114, may be prepared. The label may be prepared by using the information managed in the participant information table 122, as described above.

The feature extraction module 130 is configured to compute the feature G using a given feature function that has one or more parameters. In the learning mode, the parameter optimization module 150 is configured to optimize the parameters of the feature function such that discriminative power of the feature G is maximized over a range of the separation between the conversations.

The parameter optimization module 150 may pick up a pair of sample conversation documents of the same participant that are stored in the document storage 120 to enumerate each combination of sample documents. The parameters optimization module 150 may feed each combination of the sample documents into the feature extraction module 130. The feature extraction module 130 may output, for each combination, a trial feature G' calculated using the current value of the parameters of the feature function. The classification/regression module 140 may output a result 142 of the inference based on the trial feature G' for each combination. The parameter optimization module 150 may receive the results 142 of the inference from the classification/regression module 140 and update the parameters of the feature function by comparing each result 142 of the inference and each label associated with each combination. More detail about the parameter optimization will be described later.

In the document storage 120, a series of one or more target documents obtained from a subject user 114 is accumulated. The feature extraction module 130 is configured to compute the novel feature G for the subject by using the feature function that has the parameters optimized by the parameter optimization module 150.

In the inference mode, the report module 160 may feed at least one pair of target documents of the user 114 that corresponds to a plurality of different days into the feature extraction module 130. The feature extraction module 130 may output an extracted feature G calculated by the optimization feature function. The classification/regression module 140 may output a result 142 of the inference based on the feature G. The report module 160 may report the result 142 of the inference provided by the classification/regression module 140 to the user 114 or his/her family via an appropriate communication tool.

Note that more than two pairs of the target documents or a sequence of pairs of target documents can be used to infer the health state of the user 114 in order to improve performance and stability of the detection. In the described embodiment, the result 142 can be used to help medical diagnosis by doctors as screening for example and/or to have a good opportunity for the subject to see a doctor when necessary.

In particular embodiments, each of the modules 110, 116, 120, 122, 130, 140, 150 and 160 in the diagnosis support system 100 described in FIG. 1 may be implemented as a software module including program instructions and/or data structures in conjunction with hardware components such as a processing circuitry (e.g., a CPU (Central Processing Unit), a processing core, a GPU (Graphic Processing Unit), a FPGA (Field Programmable Gate Array)), a memory, etc.; as a hardware module including electronic circuitry (e.g., a neuromorphic chip); or as a combination thereof.

These modules 110, 116, 120, 122, 130, 140, 150 and 160 described in FIG. 1 may be implemented on a single computer system such as a personal computer and a server machine or a computer system distributed over a plurality of computing devices such as a computer cluster of computing nodes, a client-server system, a cloud computing system and an edge computing system. In a particular embodiment, the diagnosis support system 100 according to the exemplary embodiment can provide a diagnosis support service for the cognitive decline through the internet as a cloud service.

Figure 2:
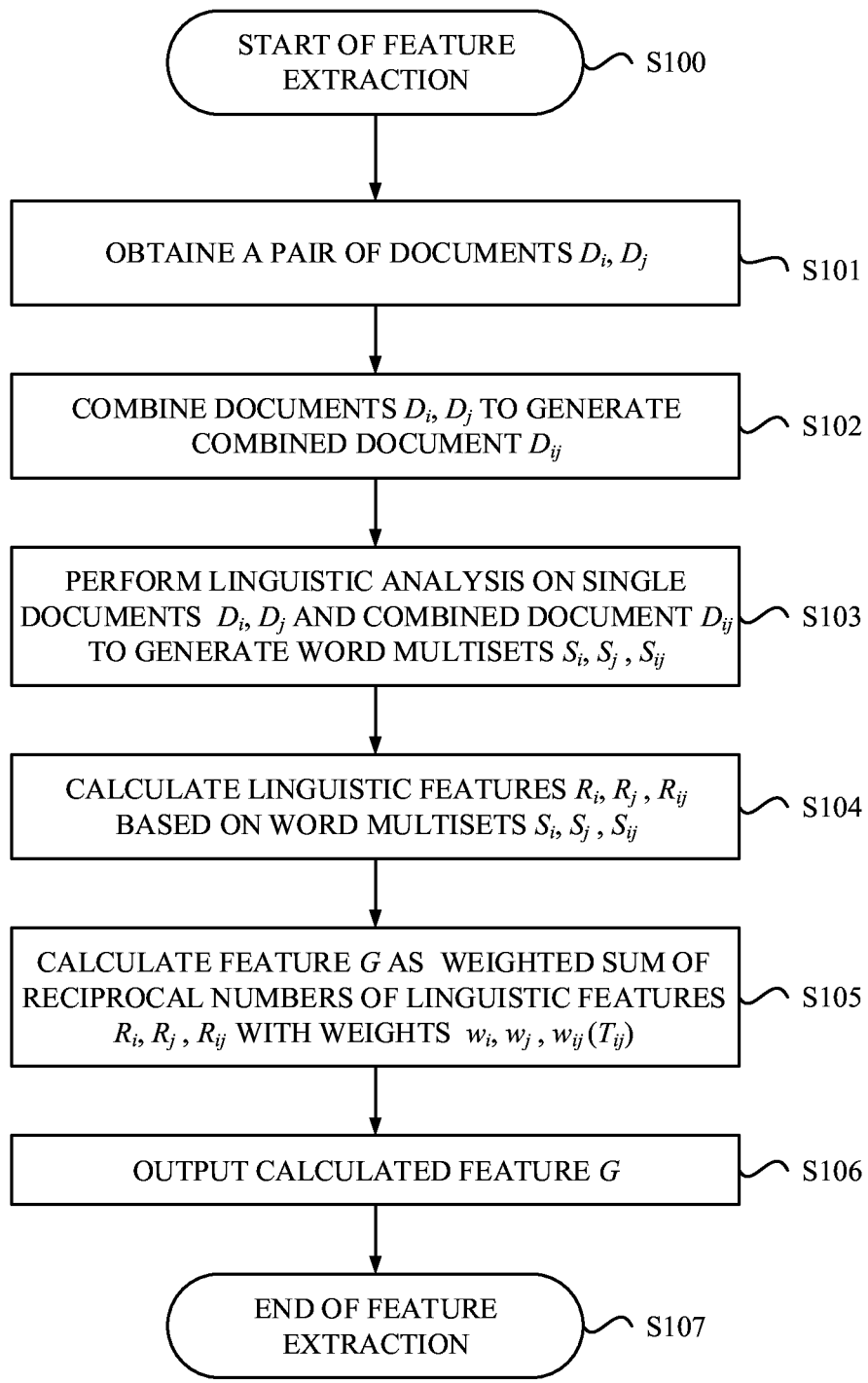
FIG. 2 is a flowchart depicting a process for extracting a feature to support a detection of cognitive decline according to an exemplary embodiment of the present invention.

With reference to FIG. 2, a process for extracting a feature to support a detection of cognitive decline according to an exemplary embodiment of the present invention is described. As shown in FIG. 2, the process may begin at step S100 in response to calling of the process of the feature extraction. Note that the process shown in FIG. 2 may be performed by processing circuitry such as a processing unit. Also note that the flow of the process shown in FIG. 2 is common in both the learning mode and the inference mode.

A step S101, the processing circuitry may obtain a pair of conversation documents $D_i$, $D_j$ of a user 114 who is a subject in the inference mode or one of the participants in the learning mode. At step S102, the processing circuitry may combine the paired conversation documents $D_i$, $D_j$ to generate a combined conversation document $D_{ij}$.

Figure 3:
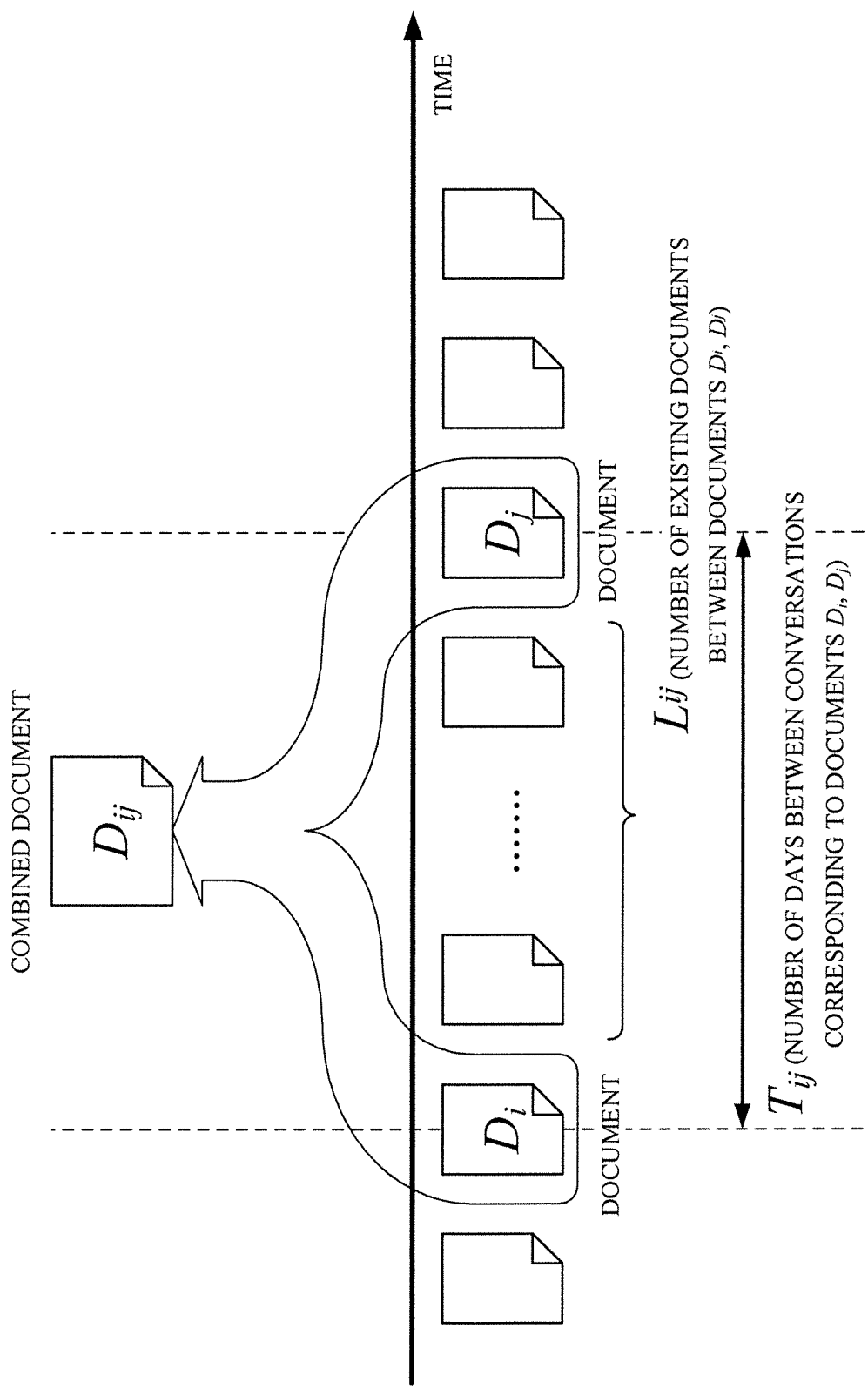
FIG. 3 describes a schematic depicting generation of a combined conversation document as preprocessing for calculating a novel feature according to the exemplary embodiment of the present invention.

Referring to FIG. 3, a schematic of way of generating a combined conversation document is described as preprocessing for calculating a novel feature G. As shown in FIG. 3, there are a series of conversation documents of an individual along time. Among these conversation documents, a pair of documents $D_i$, $D_j$ corresponding to different days is typically specified in the argument. The conversation documents $D_i$, $D_j$ specified are picked up from the document storage 120 and combined to generate a combined conversation document $D_{ij}$. The separation T between the paired documents $D_i$, $D_j$ can be measured by the number of days $T_{ij}$ between the conversations (not including the day of the first conversation but including the day of the second conversation) corresponding to the paired documents $D_i$, $D_j$ or the number of documents $L_{ij}$ existing between the paired documents $D_i$, $D_j$. In the following description, the number of days $T_{ij}$ is employed as an example.

Note that in the described embodiment, the combined conversation document $D_{ij}$ is generated from the pair of the conversation documents $D_i$, $D_j$. However, the number of documents to generate the combined conversation document may not be limited to two. In other embodiment, three or more conversation documents can be picked up and combined. Along with this modification, a separation between the furthest paired documents may be defined, for example.

Referring back to FIG. 2, at steps S103 and S104, the processing circuitry may extract three linguistic features $R_i$, $R_j$, $R_{ij}$ that represent vocabulary richness from the single conversation document $D_i$, $D_j$ and the combined conversation document $D_{ij}$.

More specifically, at step S103, the processing circuitry may perform linguistic analysis on the single documents $D_i$, $D_j$ and the combined conversation document $D_{ij}$ to generate three word multisets $S_i$, $S_j$, $S_{ij}$, respectively.

Referring to FIG. 4, a schematic of way of processing a conversation document is depicted as preprocessing for calculating the feature G.

Initially, there is an original conversation document 200 that includes one or more sentences spoken by the user 114 during a single conversation with the communicator 112. Note that the single conversation does not mean a couple of talks consisting simply of a question and a reply. The single conversation includes, but not limited to, a series of talks starting with a greeting of hello and ending with greeting of goodbye, for example. Note that example shown in FIG. 4 contains sample sentences in English, for the convenience of description, which has no connection with actual conversation.

In the linguistic analysis at step S103 of FIG. 2, at first, word segmentation/morphological analysis is performed to the original conversation document 200. In the case of language categorized in agglutinative languages such as Japanese, morphological analysis may be performed in order to segment a sentence into words. On the other hand, in the case of English and other languages that have a trivial word delimiter such as space, an original sentence is simply divided by the word delimiter to generate a series of separated words. In addition to the word segmentation, lemmatization may also be performed. After the word segmentation/morphological analysis, a segmented conversation document 210, which includes a series of separated words, is obtained.

Then, the segmented conversation document 210 is subjected to filtering to remove futile words. Such filtering may include a part-of-speech filtering and a stop word filtering. The part of speech filtering is performed to remove words that are categorized into specific parts-of-speech such as a symbol, a postpositional particle, a preposition, numeral, etc. After the part of speech filtering, a filtered conversation document 220 is obtained. The stop word filtering is performed to remove specific stop words that are considered preferable to be excluded from processing for reasons as being general. Such stop word may include "and", "but", "by", "if", "into", "such", "that", etc., in English. The stop word may include "tokoro", "aru", "kara", "na", "koto", "ya", "tame", etc., in Japanese. After the stop word filtering, there is a filtered conversation document 230, from which the word multiset is obtained finally.

Referring back to FIG. 2, at step S104, the processing circuitry may calculate three linguistic features $R_i$, $R_j$, $R_{ij}$ based on the three word multisets $S_i$, $S_j$, $S_{ij}$, respectively.

In a particular embodiment that employs the Honoré's statistic as the linguistic features R, each linguistic feature R can be calculated based on the number of words N in the word multiset S, the number of word types v in the word multiset S and the number of word types used only once u in the word multiset S. Representatively, the linguistic feature $R_{ij}$ originating from the combined conversation document $D_{ij}$ can be calculated as follows:

$$R_{ij} = HS_{ij} = \frac{100 \log N_{ij}}{1 - \frac{u_{ij}}{v_{ij}}}.$$

FIG. 5 depicts a schematic of way of calculating a linguistic feature R that represents a vocabulary richness as preprocessing for calculating the feature G. The example shown in FIG. 5 corresponds to the documents shown in FIG. 4. As shown in FIG. 5, the number of words N is calculated as the cardinality of the word multiset S, the number of word types v is calculated as the number of members in the word multiset S and the number of word types used only once u is calculated as the number of members having multiplicity 1 in the word multiset S.

Referring back to FIG. 2, at step S105, the processing circuitry may calculate the novel feature G that characterizes word repetitiveness in conversations across plural different days of the user 114 from the three linguistic features $R_i$, $R_j$, $R_{ij}$. In the preferable embodiment, the novel feature G is calculated as a weighted sum of reciprocal numbers of the linguistic features $R_i$, $R_j$, $R_{ij}$ with weights $w_i$, $w_j$, $w_{ij}$ that evaluate respective linguistic features depending upon the separation $T_{ij}$, as follows:

$$G = w_i R_i^{-1} + w_j R_j^{-1} + w_{ij} R_{ij}^{-1}.$$

$$\left( \text{where } w_{ij} = \exp\left(-\frac{(T-\mu)^2}{\sigma^2}\right), \text{ and } w_i = w_j = \frac{1 - w_{ij}}{2} \right)$$

The weight $w_{ij}$ for the combined conversation document is expressed as a weight function that has typically a form of Gaussian function with parameter $\mu$, $\sigma$. The remaining weights $w_i$, $w_j$ are set to be 1 in total together with the weight $w_{ij}$ for the combined conversation document. In the inference mode, the parameters $\mu$, $\sigma$ of the weight function has been already optimized, thus, the weights $w_i$, $w_j$, $w_{ij}$ are directly obtained from the given separation $T_{ij}$. In the learning mode, since optimized values of the parameters, $\mu$, $\sigma$ are unknown, the weight function is optimized through the parameter optimization where trial values of the weights $w_i$, $w_j$, $w_{ij}$ are tried to determine optimal values of the parameters $\mu$, $\sigma$.

At step S106, the processing circuitry may output the calculated feature G, and the process may end at step S107.

In the learning mode, the feature G calculated for one participant according to the process shown in FIG. 2 can be used as an input for the classification regression module 140 solely or in combination with other features to compare the inference result 142 with the label of the participant for answer matching. In the inference mode, the feature G calculated for one subject according to the process shown in FIG. 2 can be used as an input for a machine learning module (e.g., classification regression module 140 or other machine learning model) solely or in combination with other features to infer whether or not there is any signs of cognitive decline for the subject, or the degree of the risk of cognitive decline for the subject.

By defining the reciprocal number of the vocabulary richness measure (e.g. $HS^{-1}$) as a feature, word repetition in the single or combined document can be captured with higher resolution. Frequency of word repetition as given is not useful in the case, since words such as "I" and "am" are also counted as high repetitions regardless of the cognitive decline. Higher values of the vocabulary richness measure are obtained due to rich vocabulary used by the individual, while lower values are obtained due to their low vocabulary level. Here, the "low vocabulary level" can be considered as situation where many duplicated words and word repetitions occurs. The reciprocal number of the vocabulary richness measure can be preferably considered as a kind of the word repetition measure.

Figure 6:
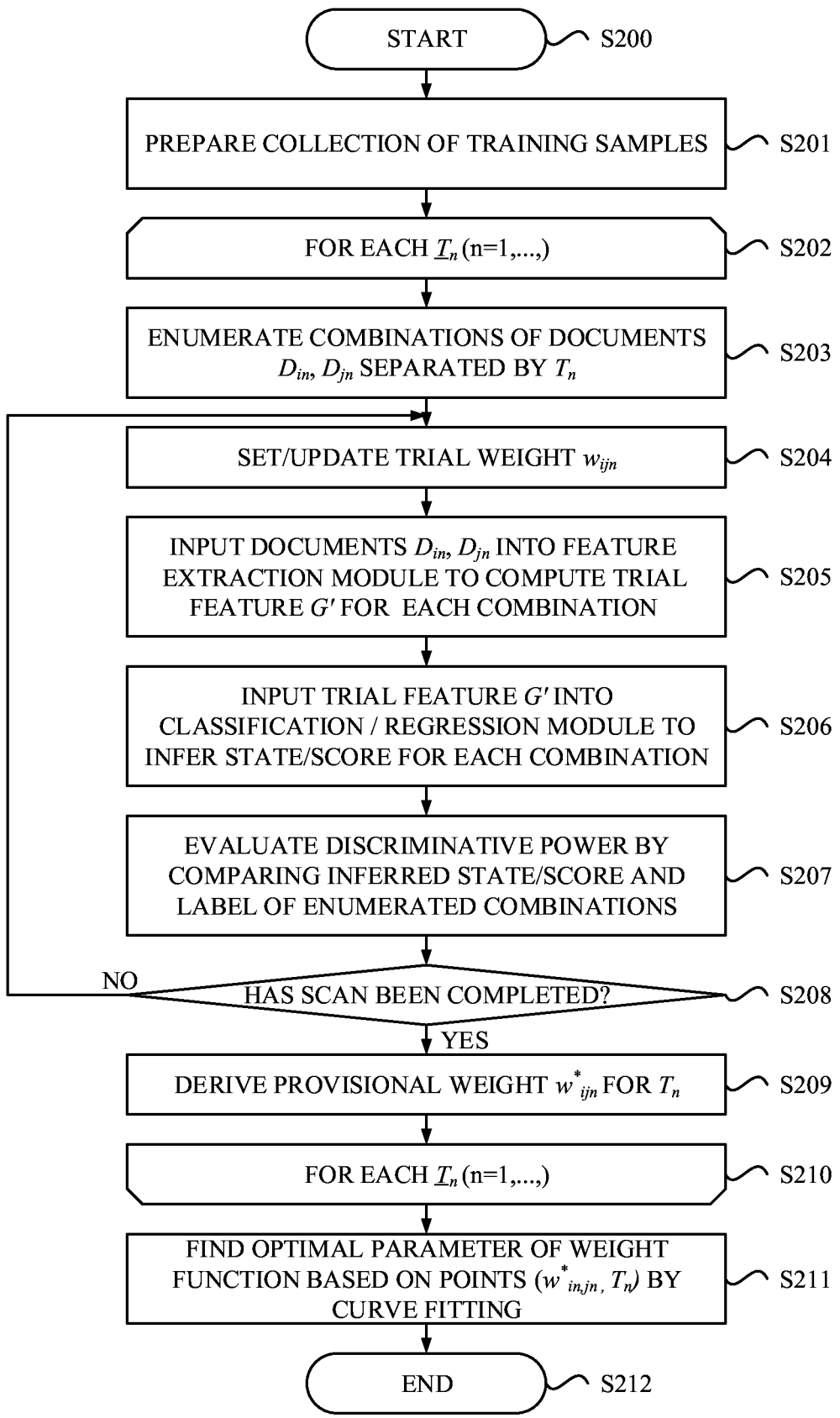
FIG. 6 is a flowchart depicting a process for optimizing a parameter of a feature function for calculating the novel feature according to an exemplary embodiment of the present invention.

With reference to FIG. 6, a process for optimizing parameters of a feature function that is used for calculating the novel feature G according to an exemplary embodiment of the present invention is described. As shown in FIG. 6, the process may begin at step S200 in response to a request of initiating a learning process from an operator. Note that the process shown in FIG. 6 may be performed by processing circuitry such as a processing unit.

A step S201, the processing circuitry may prepare a collection of training samples, each of which includes one or more sample conversation documents of a participant with a corresponding label. The loop from step S202 to step S210 are repeatedly performed for each interval of the separation $T_n$ (n=1, 2, . . . ). In the described embodiment, a whole range of the separation T is divided by day and thus the interval $T_n$ represents directly the number of days between the two conversations.

At step S203, the processing circuitry may enumerate, for each interval of the separation $T_n$, a plurality of combinations based on the collection of the training samples. Each enumerated combination includes a paired sample conversation documents $D_{in}$, $D_{jn}$ of the same participant separated by days categorized into the interval $T_n$ (that is, $T_n$ days in the described embodiment).

The loop from the step S204 to step S208, the weight $w_{ij}$ (and also remaining weights $w_i$, $w_j$) is varied to calculate trial results of the feature G for every trial values of the weight $w_{ij}$.

At step S204, the processing circuitry may set a trial value of the weight (the trial weight for $T_n$ is denoted as $w_{ijn}$) In a particular embodiment, the trial weight $w_{ijn}$ may be varied from 0 to 1 during the scanning. At step S205, the processing circuitry may input the pair of the sample conversation documents $D_{in}$, $D_{jn}$ into the feature extraction module 130 to compute the trial feature G' for each combination.

In the process shown in step S205, the paired sample conversation documents $D_{in}$, $D_{jn}$ for each combination are combined to generate a combined sample document $D_{injn}$ and three linguistic features $R_{in}$, $R_{jn}$, $R_{injn}$ are extracted from the single and combined sample documents $D_{in}$, $D_{jn}$, $D_{injn}$. The trial result of the feature G' is computed from the linguistic features $R_{in}$, $R_{jn}$, $R_{injn}$ using a current version of the feature function that is characterized by the specific value of the weight $w_{ijn}$.

At step S206, the processing circuitry may input the computed trial feature G' into the classification/regression module 140 to infer the state/score of the cognitive decline for each combination. In a particular embodiment with binary classification, appropriate cut off value is set. At step S207, the processing circuitry may evaluate discriminative power by comparing inferred state/scores and labels for all combinations enumerated for the interval $T_n$. In a particular embodiment with binary classification, ROC (Receiver Operator Curve)-AUC (Area Under the Curve) and/or effect size can be used to evaluate the discriminative power.

At step S208, the processing circuitry may determine whether or not the scanning of trial weight $w_{ijn}$ has been completed. If the weight $w_{ijn}$ has been varied from 0 to 1, for example, the scanning is determined to be completed. In response to determining that the scanning of the weight has not been completed yet (S208: NO), the process may loop back to step S204 for another trial. On the other hand, in response to determining that the scanning of the weight has completed (S208: YES), the process may proceed to step S209.

A step S209, the processing circuitry may derive a provisional value $w_{ijn}*$ showing highest discriminative power for each interval of the separation $T_n$.

After exiting the loop from step S202 to step S210, the process may proceed to step S211. When exiting from the loop, the provisional weights $w_{ijn}*$ for all intervals of the separation $T_n$ (n=1, 2, . . . ) have been obtained. At step S211, the processing circuitry may perform curve fitting on data points, each of which is represented by the provisional value of the weight $w_{ijn}*$ and the interval of the separation $T_n$, to find an optimal value of the parameters σ, μ of the weight function. The process may end at step S212. The parameters of the feature extraction module 130 are updated to optimal one according to the process shown in FIG. 6.

Figure 7:
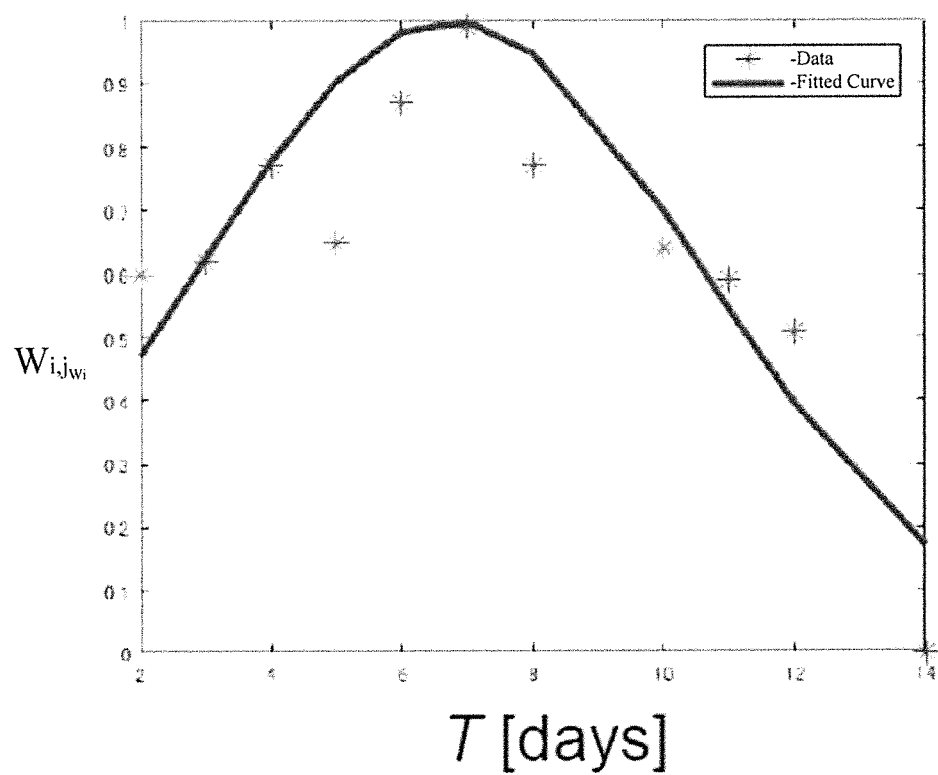
FIG. 7 illustrates a plot showing an optimal weight where the maximized discriminative power was obtained for each separation between the conversations with a fitted curve.

FIG. 7 illustrates a plot showing an optimal weight $w_{ijn}*$ where the maximized discriminative power (AUC-ROC) was obtained for each separation between the conversations $T_n$ (n=1, 2, . . . ). Note that the real sample data points obtained experimentally and the fitted curve fit to the real sample data points are displayed in FIG. 7. Detail of the experimental study will be described later.

Figure 8:
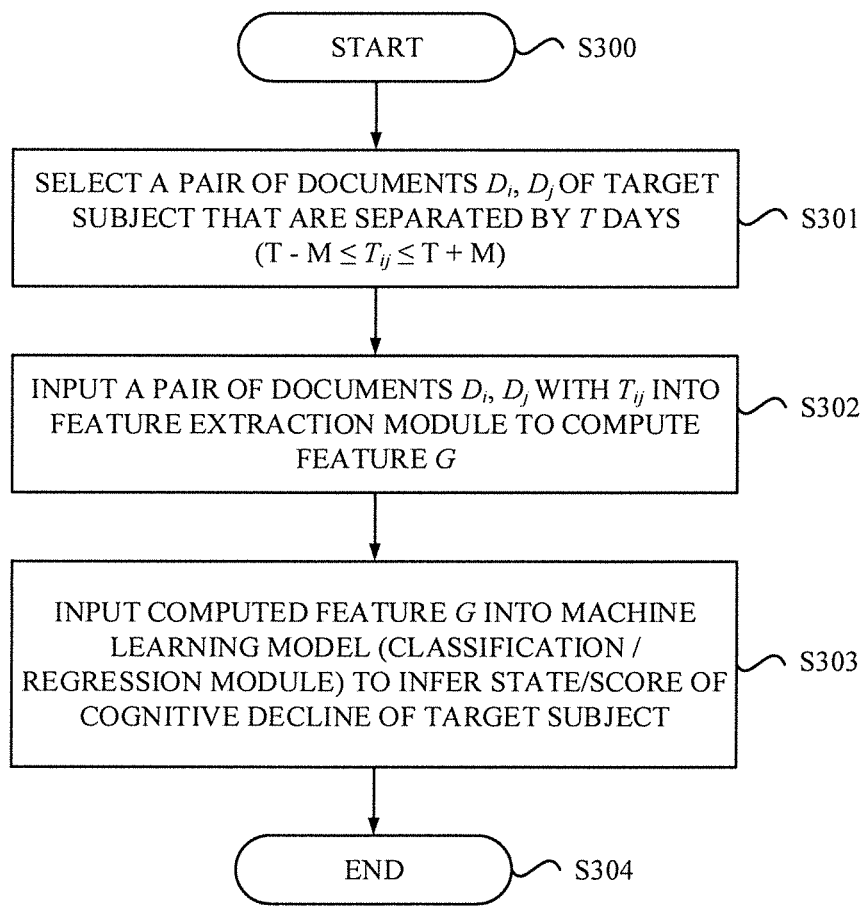
FIG. 8 is a flowchart depicting a process for detecting a sign of cognitive decline using the novel feature according to an exemplary embodiment of the present invention.

With reference to FIG. 8, a process for detecting a sign of cognitive decline using the novel feature G according to an exemplary embodiment of the present invention is described. As shown in FIG. 8, the process may begin at step S300 in response to a request for initiating a detection process for a target subject from his/her family member, for example. Note that the process shown in FIG. 8 may be performed by processing circuitry such as a processing unit.

At step S301, the processing circuitry may select a pair of conversation documents $D_i$, $D_j$ of the target subject that are separated by almost T days with an appropriate margin M (T−M≤$T_{ij}$≤T+M). Since higher discriminative power can be obtained when the number of days T between the conversations is ranging from 6 to 8 days, thus the pair of the target documents is preferably selected in such a way.

At step S302, the processing circuitry may input the selected pair of the conversation documents $D_i$, $D_j$ with the separation $T_{ij}$ into the feature extraction module 130 to compute the feature G.

In the process shown in step S302, the paired conversation documents $D_i$, $D_j$ are combined to generate a combined document $D_{ij}$ and three linguistic features $R_i$, $R_j$, $R_{ij}$ are extracted from the single and combined documents $D_i$, $D_j$, $D_{ij}$. The feature G is computed from the linguistic features $R_i$, $R_j$, $R_{ij}$ with weights $w_i$, $w_j$, $w_{ij}$ that are calculated from the separation $T_{ij}$ using the optimized weight function.

At step S303, the processing circuitry may input the computed feature G into the machine learning model (the classification/regression module 140) to infer the state/score of the cognitive decline of the target subject and the process ends at step S304.

Note that, in the inference model, the machine learning model used to infer the state/score of the cognitive decline may be same as or different from the classification/regression module 140 used to evaluate the discriminative power in the training mode. For example, the parameters of the feature extraction module 130 are optimized by using a simple binary classifier based solely on the feature G in the training mode. In the inference mode, the feature G can be used as an input for other sophisticated machine learning model such as deep neural network in combination with other feature.

According to one or more embodiments of the present invention, the feature suitable for detecting a sign of cognitive decline can be computed from the conversation documents of the target individual. Leveraging the specially designed feature can lead a performance improvement for detecting the sign of the cognitive decline. Since the feature has larger discriminative power, i.e., the distribution of the features for the control group and the distribution of the features for the patient group are preferably separated, even simple classifiers that do not require so many computational resources can classifier well based on the feature. Enriching of features that can be used to detect the sign of the cognitive decline can reduce the computational resources by way of (1) providing an efficient feature set composed of fewer features and/or (2) providing a model having higher generalization performance to avoid the need for building models individually and specifically designed for each individual and for each situation.

In the typical monitoring service, practically, it is difficult to obtain conversation data at predetermined regular intervals due to user's circumstances. By weighting the linguistic feature depending upon the separation, the sets of the conversation data even that has such variation can be utilized without being wasted, and can be evaluated by taking such variation of the separation into account.

Note that the languages to which the novel feature extraction technique is applicable is not limited and such languages may include, but by no means limited to, Arabic, Chinese, English, French, German, Japanese, Korean, Portuguese, Russian, Spanish, for instance.

EXPERIMENTAL STUDIES

A program implementing modules 120, 122, 130, 140, 150 of the system indicated by the rectangle with a dashed border in FIG. 1 and the process shown in FIG. 2, FIG. 6, and FIG. 8 according to the exemplary embodiment was coded and executed for given sample documents.

The sample documents were plural sets of daily conversation data obtained from a monitoring service for elderly people. The purpose of this service is to help children to build a connection with their parent living alone by sharing the daily life information of elderly people, such as their physical condition. The communicator called elderly people once or twice a week to have a daily conversation for about ten minutes. Each conversation was transcribed in spoken word format by the communicator and sent to the family by email. The spoken words of the communicator were eliminated. The conversational data were collected from eight Japanese people (five females and three males; age range 66-89 years, i.e., 82.37±5.91 years old). Two of them were reported as suffering from dementia from the family.

In total, 458,738 words were used for the analysis. All reports were written in Japanese. For preprocessing, linguistic analysis including word segmentation, part-of-speech tagging and word lemmatization on the conversation data were performed. The words tagged as numerals and symbols were excluded from the analyzing data. For the preprocessing, the Japanese morphological analyzer MeCab was utilized (T. Kudo. Mecab: Yet another part-of-speech and morphological analyzer. http://mecab.sourceforge.net/, 2005.)

As for Examples and Comparative examples, the proposed feature G and other conventional features were investigated using the conversational data obtained during the phone calls with the regular monitoring service. The discriminative power was measured by using both effect size (Cohen's d) and area under the receiver operating characteristic curve (AUC-ROC). For Cohen's d, the 0.8 effect size can be assumed to be large, while the 0.5 effect size is medium and the 0.2 effect size is small. ROC is a graphical plot that illustrates the diagnostic ability of a binary classifier model that ranges from 0 to 1.

As for Example 1, the feature G was calculated from sample conversation documents that were separated by T days in addition to a single conversations conducted within a single day. The Honoré statistic (HS) was used as the linguistic feature R for each conversation document. The hyper-parameters $w_i$, $w_j$, $w_{ij}$ for the T=8 was set to be 0.125, 0.125, and 0.75, respectively, which were selected by the parameter optimization.

As a result, it was found that the proposed feature G for people with dementia was significantly higher than that of controls (p<1.0×10-24). The effect size of 2.68 (95% confidential interval (CI): 2.11-3.25) and the AUC-ROC of 0.97 were obtained.

As Comparative Examples 1-5, other features extracted from single conversation, including vocabulary richness, sentence complexity, and repetitiveness, were also investigated. As for vocabulary richness, Type-token ratio (Comparative Example 1), Brunet's index (Comparative Example 2) and Honoré's statistic (Comparative Example 3) were used. For sentence complexity and repetitiveness, mean sentence length (Comparative Example 4) and sentence similarity (Comparative Example 5) were employed, respectively. The sentence similarity was computed using cosine distance of sentences defined as TF-IDF (Term Frequency-Inverse Document Frequency) vectors.

Figure 9:
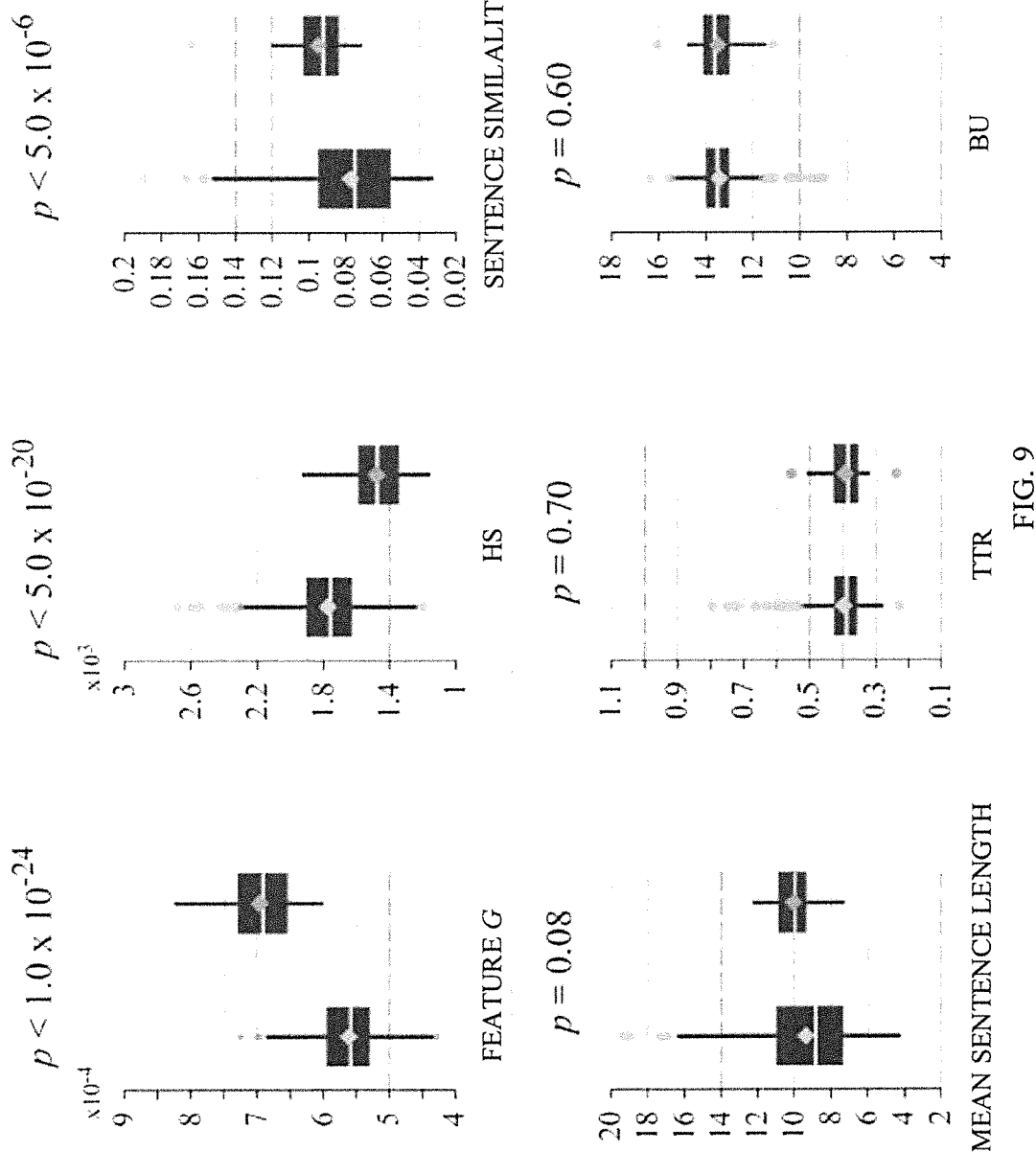
FIG. 9 depicts feature distributions for control and dementia in the proposed feature G and the other conventional five features.
Figure 10:
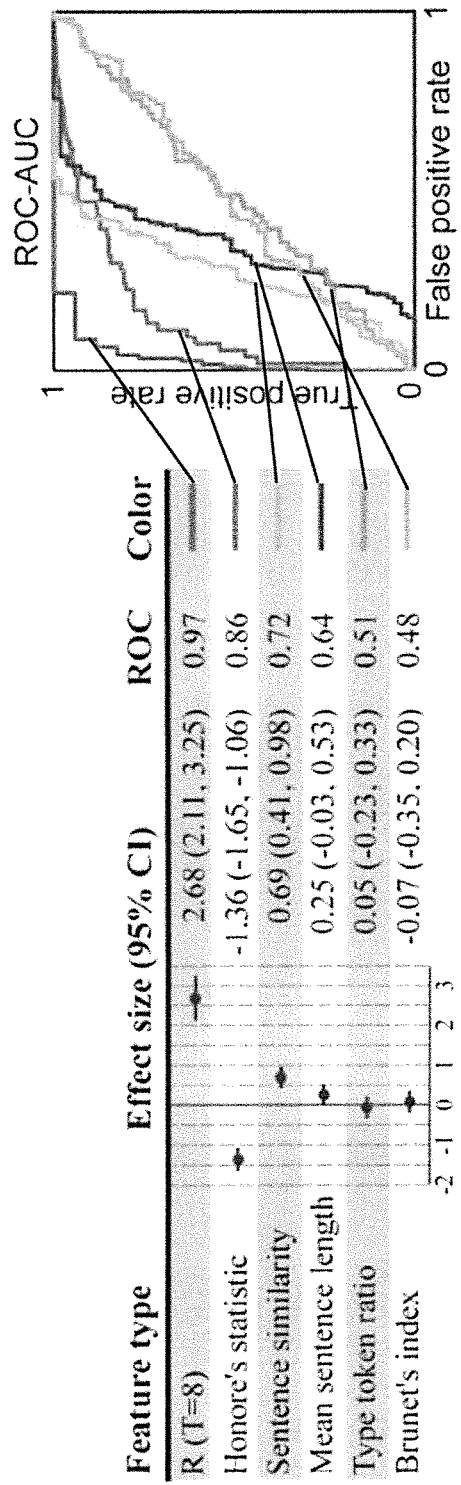
FIG. 10 shows comparison of the proposed feature G with the conventional five features.

FIG. 9 depicts feature distributions for control and dementia in the proposed feature G and the other conventional five features. In FIG. 9, boxes denote the 25th (Q1) and 75th (Q3) percentiles. The line within the box denotes the 50th percentile, while whiskers denote the upper and lower adjacent values that are the most extreme values within Q3+1.5(Q3-Q1) and Q1-1.5(Q3-Q1), respectively. Filled circles show outliers, and squares represent mean values. FIG. 10 shows comparison of the proposed feature G with the conventional five features. In FIG. 10, error bars are 95% confidence intervals (CI).

Among the six features (Example 1, Comparative Examples 1-5), significant differences between control and dementia was observed in three features: the proposed feature G (Example 1), Honoré's statistic (Comparative Example 3) and sentence similarity (Comparative Example 5) ($p<1.0\times10^{-24}$, $p<5.0\times10^{-20}$, $p<5.0\times10^{-6}$, respectively), as shown in FIG. 9. In contrast, the type-token ratio (Comparative Example 1), the Brunet's index (Comparative Example 2) and the mean sentence length (Comparative Example 4) had no significant difference between the groups (p>0:05). The proposed feature G (Example 1) showed the best results in terms of effect size and ROC (d=2.68, ROC=0.97), followed by Honoré's Statistic (Comparative Example 3) (d=−1.36, ROC=0.86), and the sentence similarity (Comparative Example 5) (d=0.69, ROC=0.72) as shown in FIG. 10.

Since the proposed feature G aims to characterize word repetition, especially in conversations on different days in addition to a single conversation on a single day, the usefulness of the feature representing the repetition in conversation on different days was also investigated. As for Example 2, the feature $HS_{ij}^{-1}$ was calculated from merely combined document of two sample documents of conversations that were separated by T days. As for Comparative Example 6, the feature $HS_i^{-1}$ was calculated from a sample document corresponding to a single conversation conducted within a single day.

The feature $HS_{ij}^{-1}$ calculated from the combined sample document showed the effect size of 2.67 (95% confidential interval (CI): 2.10-3.24) and the AUC-ROC of 0.96. The feature $HS_i^{-1}$ calculated from the single sample document showed the effect size of 1.58 (95% confidential interval (CI): 1.28-1.88) and the AUC-ROC of 0.86. The results are summarized in Table 1.

TABLE 1

| Feature type | Effect Size (95% CI) | AUC-ROC |
|---|---|---|
| combined document ($D_{ij}$) with single documents ($D_i$, $D_j$) (Example 1) | 2.68 (2.11, 3.25) | 0.97 |
| Merely combined document ($D_{ij}$) (Example 2) | 2.67 (2.10-3.24) | 0.96 |
| single document ($D_i$, $D_j$) (Comparative Example 6) | 1.58 (1.28, 1.88) | 0.86 |

The feature $HS_{ij}^{-1}$ extracted from the paired conversations and the feature $HS_i^{-1}$ extracted from the single conversation both showed significant differences between the control and the dementia ($p<1.0\times10^{-6}$ for the single conversation; $p<1.0\times10^{-24}$ for the paired conversation). The features $HS_{ij}^{-1}$ extracted from the paired conversations had larger discriminative power than the feature $HS_i^{-1}$ extracted from the single conversations in terms of the effect size and the ROC score. The results suggest that the feature part extracted from the paired conversational data contributes to detection performance of the proposed feature G.

Figure 11:
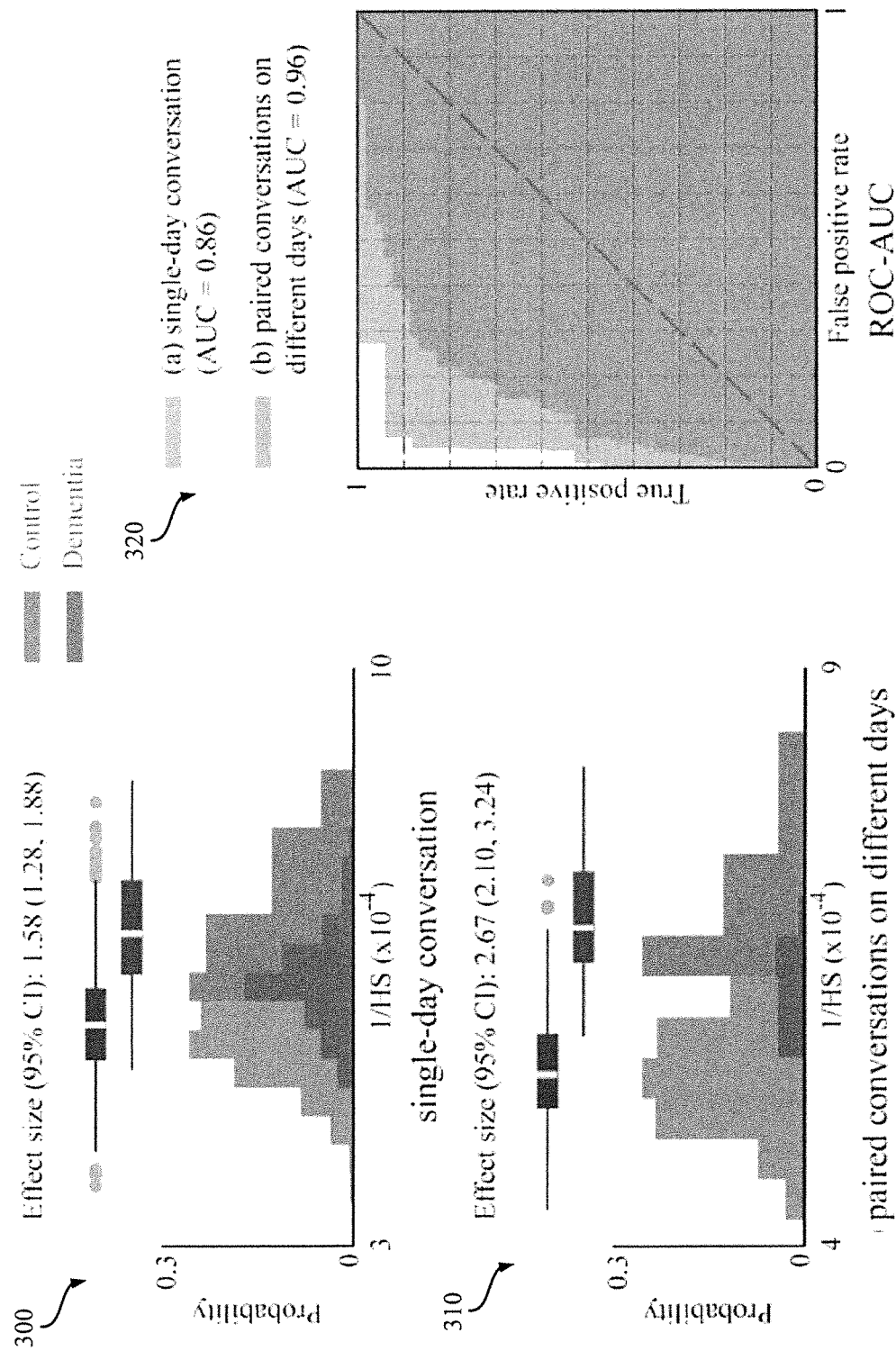
FIG. 11 shows comparison between the proposed features G extracted from single and paired conversations.

FIG. 11 shows comparison between the proposed features G extracted from the single and paired conversations. FIG. 11 shows histograms 300, 310 with boxplot for each feature and a AUC-ROC graphical plot 320. As shown in the histograms 300, 310 of FIG. 11, the distribution of the features for the control group and the distribution of the features for the patient group are preferably separated when the features $HS_{ij}^{-1}$ extracted from the paired conversations are employed.

Figure 12:
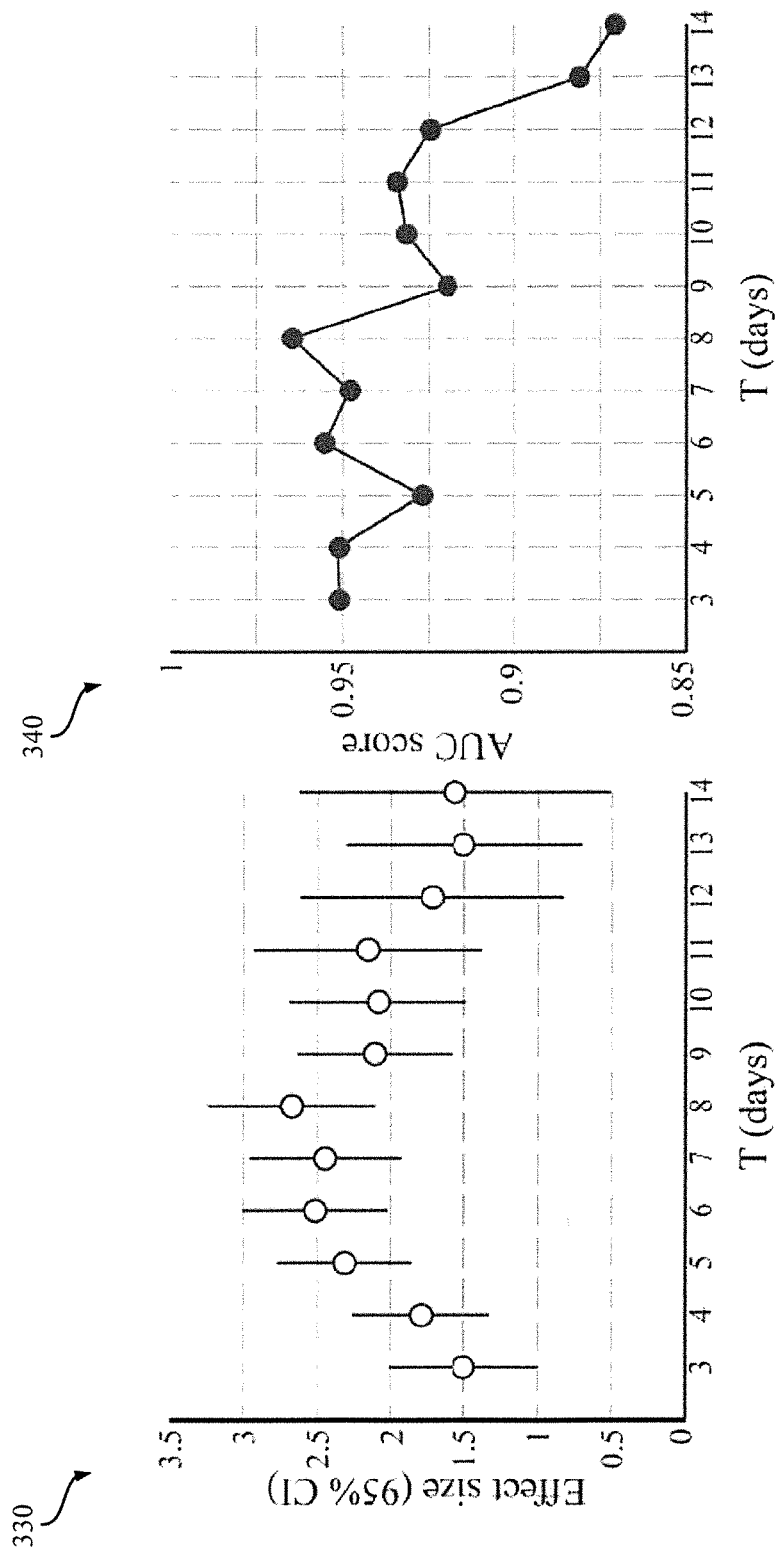
FIG. 12 shows the effect size and the AUC of the proposed feature G with the separation T.

As further other Example 3, the tendency of the proposed feature G with different intervening days of paired conversations was investigated. Specifically, the discriminative power of the feature G extracted from the paired conversation was compared by changing T from 3 to 14 days (not including the day of the first conversation but including the day of the second conversation). In the Example 3, the weight $w_{ij}$ was set to 1 and others $w_i$, $w_j$ as 0 for simplicity. In all T values calculated in this study, the proposed feature G for people with dementia was significantly higher than that of controls ($p<0.05$). FIG. 12 shows the effect size and the AUC of the proposed feature G with the separation T. As shown in the graphs 330, 340 of FIG. 12, the effect size and the AUC-ROC values respectively ranged from 1.5 to 2.67 and from 0.87 to 0.96. After they increased in the beginning, they peaked at around T=8 (effect size of 2.67, 95% CI: 2.10-3.24; ROC=0.96) and had a tendency to decline as shown in FIG. 12.

As further other Example 4, the parameter optimization process shown in FIG. 6 was conducted by using the sample documents. An optimal weights $w_{ijn}*$ that maximized the discriminative power (AUC-ROC) were calculated for every separations $T_n$ in the range from 2 to 14 days. FIG. 7 shows a plot of data points, each of which is represented by the optimal weight $w_{ijn}*$ and the separations $T_n$. As shown in FIG. 7, the plot shows that there is a peak around $T_{ij}$=7 days. The parameters $\mu$ and $\sigma$ of the fitted curve shown in FIG. 7 were estimated to be 8.7 and 5.5, respectively. The profile of the curve rendered by the data points indicates appropriate weight $w_{ij}$ that provides maximum discriminative power for each separation T. It means that the maximum discriminative power is expected to be obtained by setting $w_{ij}$ to be a specific value on the curve at T=2 when merely conversation documents that are obtained every other day are available, for example.

As described above, it was found that the proposed feature G has strong discriminating power and achieved up to 2.68 for effect size of Cohen's d and 0.97 for AUC-ROC scores. It was also demonstrated that the proposed feature G outperformed other conventional features, suggesting that the use of the proposed feature G in addition to the conventional features has promise to improve detection performance. Based on the analysis on the feature extracted from the single conversational data and the paired conversational data, it was shown that the features from paired conversations on different days may be more advantageous in increasing discriminative power than extracting them from a single day conversation. In addition, the results obtained in changing the intervening days of two separate conversational data suggest that the proposed feature G could be especially useful when extracted from conversations of the specific intervening days, which is expected to be related to the memory mechanism of the brain.

Computer Hardware Component

Figure 13:
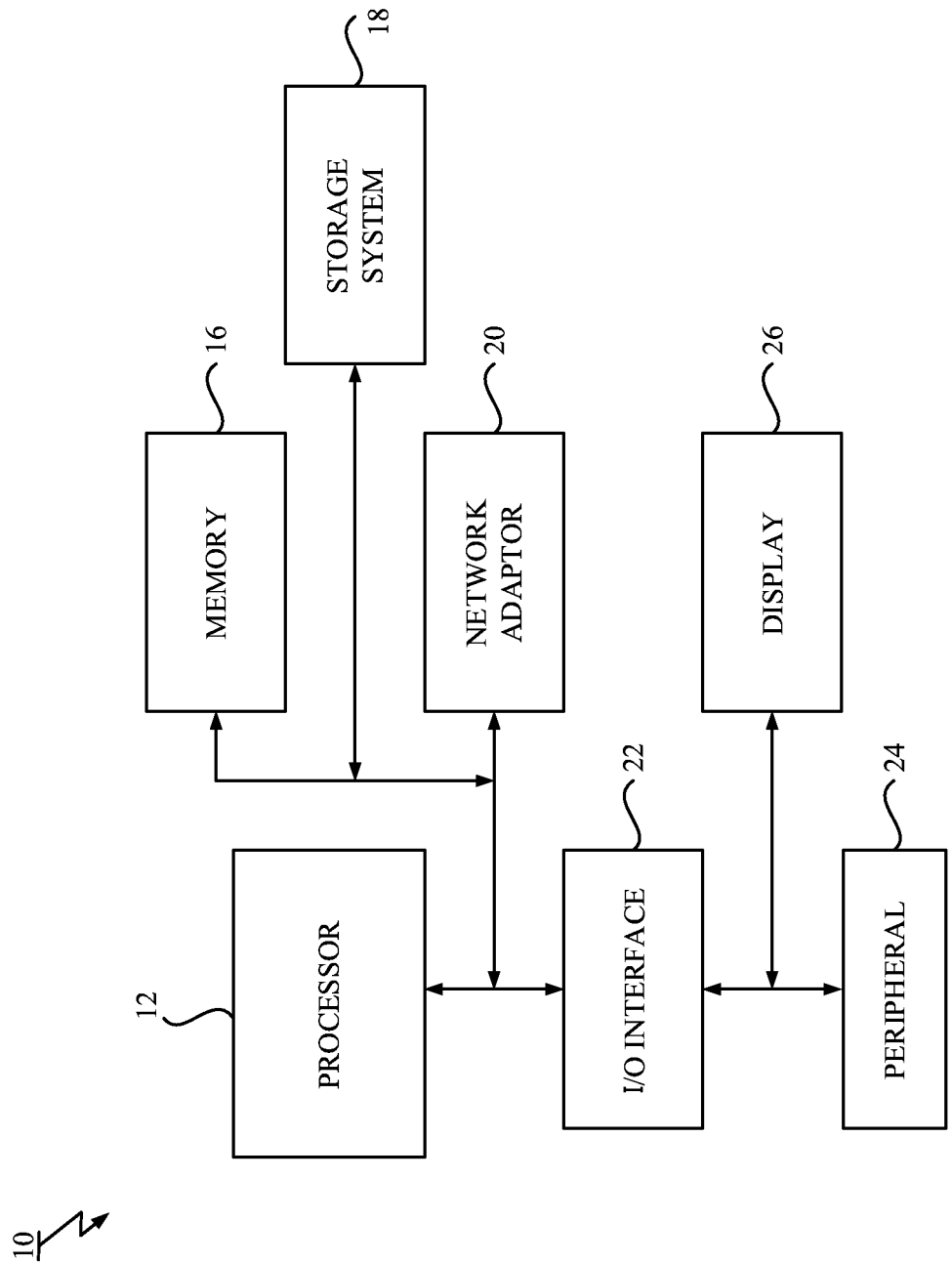
FIG. 13 depicts a computer system according to one or more embodiment of the present invention.

Referring now to FIG. 13, a schematic of an example of a computer system 10, which can be used for the diagnosis support system 100, is shown. The computer system 10 shown in FIG. 13 is implemented as computer system. The computer system 10 is only one example of a suitable processing device and is not intended to suggest any limitation as to the scope of use or functionality of embodiments of the invention described herein. Regardless, the computer system 10 is capable of being implemented and/or performing any of the functionality set forth hereinabove.

The computer system 10 is operational with numerous other general purpose or special purpose computing system environments or configurations. Examples of well-known computing systems, environments, and/or configurations that may be suitable for use with the computer system 10 include, but are not limited to, personal computer systems, server computer systems, thin clients, thick clients, handheld or laptop devices, in-vehicle devices, multiprocessor systems, microprocessor-based systems, set top boxes, programmable consumer electronics, network PCs, minicomputer systems, mainframe computer systems, and distributed cloud computing environments that include any of the above systems or devices, and the like.

The computer system 10 may be described in the general context of computer system-executable instructions, such as program modules, being executed by a computer system. Generally, program modules may include routines, programs, objects, components, logic, data structures, and so on that perform particular tasks or implement particular abstract data types.

As shown in FIG. 13, the computer system 10 is shown in the form of a general-purpose computing device. The components of the computer system 10 may include, but are not limited to, a processor (or processing unit) 12 and a memory 16 coupled to the processor 12 by a bus including a memory bus or memory controller, and a processor or local bus using any of a variety of bus architectures.

The computer system 10 typically includes a variety of computer system readable media. Such media may be any available media that is accessible by the computer system 10, and it includes both volatile and non-volatile media, removable and non-removable media.

The memory 16 can include computer system readable media in the form of volatile memory, such as random access memory (RAM). The computer system 10 may further include other removable/non-removable, volatile/non-volatile computer system storage media. By way of example only, the storage system 18 can be provided for reading from and writing to a non-removable, non-volatile magnetic media. As will be further depicted and described below, the storage system 18 may include at least one program product having a set (e.g., at least one) of program modules that are configured to carry out the functions of embodiments of the invention.

Program/utility, having a set (at least one) of program modules, may be stored in the storage system 18 by way of example, and not limitation, as well as an operating system, one or more application programs, other program modules, and program data. Each of the operating system, one or more application programs, other program modules, and program data or some combination thereof, may include an implementation of a networking environment. Program modules generally carry out the functions and/or methodologies of embodiments of the invention as described herein.

The computer system 10 may also communicate with one or more peripherals 24 such as a keyboard, a pointing device, a car navigation system, an audio system, etc.; a display 26; one or more devices that enable a user to interact with the computer system 10; and/or any devices (e.g., network card, modem, etc.) that enable the computer system 10 to communicate with one or more other computing devices. Such communication can occur via Input/Output (I/O) interfaces 22. Still yet, the computer system 10 can communicate with one or more networks such as a local area network (LAN), a general wide area network (WAN), and/or a public network (e.g., the Internet) via the network adapter 20. As depicted, the network adapter 20 communicates with the other components of the computer system 10 via bus. It should be understood that although not shown, other hardware and/or software components could be used in conjunction with the computer system 10. Examples, include, but are not limited to: microcode, device drivers, redundant processing units, external disk drive arrays, RAID systems, tape drives, and data archival storage systems, etc.

Computer Program Implementation

The present invention may be a computer system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components and/or groups thereof.

The corresponding structures, materials, acts, and equivalents of all means or step plus function elements in the claims below, if any, are intended to include any structure, material, or act for performing the function in combination with other claimed elements as specifically claimed. The description of one or more aspects of the present invention has been presented for purposes of illustration and description, but is not intended to be exhaustive or limited to the invention in the form disclosed.

Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method for supporting detection of a sign of cognitive decline, the method comprising:
    obtaining two or more sets of conversation data of a target individual;
    combining at least two sets of the conversation data corresponding to a plurality of different days to generate a combined set;
    extracting one or more linguistic features representing vocabulary richness from at least the combined set;
    calculating a feature characterizing word repetitiveness in conversations across the plurality of different days of the target individual using weights applied to the one or more linguistic features; and
    inferring whether or not there is the sign of cognitive decline, or the degree of the risk of the cognitive decline, using the feature characterizing word repetitiveness as an input for a machine learning model.

2. The method of claim 1, wherein the one or more linguistic features include a first linguistic feature extracted from the combined set and one or more other linguistic features each extracted from one of the two or more sets of the conversation data.

3. The method of claim 2, wherein the one or more other linguistic features include a second linguistic feature extracted from one of the at least two sets of the conversation data and a third linguistic feature extracted from another of the at least two sets of the conversation data.

4. The method of claim 2, wherein the feature characterizing word repetitiveness is calculated as a weighted sum of reciprocal numbers of the first linguistic feature and the one or more other linguistic features.

5. The method of claim 2, wherein both the first linguistic feature and the one or more other linguistic features are Honoré's statistics.

6. The method of claim 1, wherein the feature characterizing word repetitiveness is calculated by using a weight for evaluating the linguistic features depending upon a separation between conversations corresponding to the combined at least two sets of conversation data.

7. The method of claim 6, wherein the weight is defined by a weight function having a parameter, the weight function being optimized by:
    preparing one or more training samples each including one or more sample sets of conversation data of a participant and a label regarding the cognitive decline;
    enumerating a plurality of combinations based on the one or more training samples, each combination including at least two sample sets of the conversation data corresponding to a plurality of different days of the same participant with a corresponding label for the at least two sample sets; and
    finding an optimal value of the parameter of the weight function based on the plurality of combinations by maximizing discriminative power given by the feature characterizing word repetitiveness, the discriminative power being evaluated by using the corresponding label in each combination.

8. The method of claim 7, wherein one or more combinations are enumerated for each interval of the separation in a range, wherein finding the optimal value of the parameter of the weight function comprises:
varying, for each interval of the separation, a trial value of the weight to calculate trial results of the feature characterizing word repetitiveness based on at least a combined sample set generated from the at least two sample sets of the conversation data in each combination enumerated for the interval of the separation;
deriving, for each interval of the separation, a provisional value of the weight showing a highest discriminative power based on the trial results of the feature characterizing word repetitiveness calculated for the interval of the separation; and
performing curve fitting on data points each represented by the provisional value of the weight and the interval of the separation to obtain the optimal value of the parameter of the weight function.

9. The method of claim 6, wherein the separation is measured by the number of days between the conversations corresponding to the at least two sets or the number of sets existing between the at least two sets.

10. The method of claim 1, wherein extracting the one or more linguistic features comprises:
performing linguistic analysis on the combined set to obtain a word multiset for the combined set; and
calculating a first linguistic feature for the combined set based on the number of words in the word multiset, the number of word types in the word multiset and the number of word types having multiplicity in the word multiset.

11. The method of claim 1, wherein the number of days between the conversations is ranging from 6 to 8 days.

12. A computer system for supporting detection of a sign of cognitive decline, by executing program instructions, the computer system comprising:
a memory tangibly storing the program instructions;
a processor in communication with the memory, wherein the processor is configured to:
obtain two or more sets of conversation data of a target individual;
combine at least two sets of the conversation data corresponding to a plurality of different days to generate a combined set;
extract one or more linguistic features representing vocabulary richness from at least the combined set;
calculate a feature characterizing word repetitiveness in conversations across the plurality of different days of the target individual using weights applied to the one or more linguistic features; and
infer whether or not there is the sign of cognitive decline, or the degree of the risk of the cognitive decline, using the feature characterizing word repetitiveness as an input for a machine learning model.

13. The computer system of claim 12, wherein the feature characterizing word repetitiveness is calculated by using a weight for evaluating the linguistic features depending upon a separation between conversations corresponding to the combined at least two sets of conversation data.

14. The computer system of claim 12, wherein the one or more linguistic features include a first linguistic feature extracted from the combined set and one or more other linguistic features each extracted from one of the two or more sets of the conversation data.

15. The computer system of claim 14, wherein the feature characterizing word repetitiveness is calculated as a weighted sum of reciprocal numbers of the first linguistic feature and the one or more other linguistic features.

16. A computer program product for supporting detection of a sign of cognitive decline, the computer program product comprising a computer readable storage medium having program instructions embodied therewith, the program instructions executable by a computer to cause the computer to perform a method comprising:
obtaining two or more sets of conversation data of a target individual;
combining at least two sets of the conversation data corresponding to a plurality of different days to generate a combined set;
extracting one or more linguistic features representing vocabulary richness from at least the combined set;
calculating a feature characterizing word repetitiveness in conversations across the plurality of different days of the target individual using weights applied to the one or more linguistic features; and
inferring whether or not there is the sign of cognitive decline, or the degree of the risk of the cognitive decline, using the feature characterizing word repetitiveness as an input for a machine learning model.

17. The computer program product of claim 16, wherein the feature characterizing word repetitiveness is calculated by using a weight for evaluating the linguistic features depending upon a separation between conversations corresponding to the combined at least two sets of conversation data.

* * * * *